United States Patent
DiBella

(10) Patent No.: US 7,906,467 B2
(45) Date of Patent: *Mar. 15, 2011

(54) ANTIOXIDANTS FOR SYNTHETIC LUBRICANTS AND METHODS OF MANUFACTURE

(75) Inventor: Eugene P. DiBella, Newton, NJ (US)

(73) Assignee: Chemtura Corporation, Middlebury, CT (US)

( * ) Notice: Subject to any disclaimer, the term of this patent is extended or adjusted under 35 U.S.C. 154(b) by 737 days.

This patent is subject to a terminal disclaimer.

(21) Appl. No.: 11/923,250

(22) Filed: Oct. 24, 2007

(65) Prior Publication Data

US 2008/0194445 A1 Aug. 14, 2008

Related U.S. Application Data

(63) Continuation of application No. 11/672,559, filed on Feb. 8, 2007, now Pat. No. 7,307,049.

(51) Int. Cl.
    C10M 129/68 (2006.01)
    C10M 133/06 (2006.01)
    C08K 5/18 (2006.01)
    C07C 211/43 (2006.01)

(52) U.S. Cl. ........ 508/459; 508/508; 508/545; 564/429; 524/256

(58) Field of Classification Search ............... 508/459, 508/545, 508; 564/429; 524/256
    See application file for complete search history.

(56) References Cited

U.S. PATENT DOCUMENTS

| 3,492,233 | A | 1/1970 | Hepplewhite et al. | |
|---|---|---|---|---|
| 3,509,214 | A * | 4/1970 | Braid et al. | 564/308 |
| 3,773,665 | A * | 11/1973 | Braid | 508/184 |
| 4,440,657 | A | 4/1984 | Metro et al. | |
| 5,049,290 | A | 9/1991 | Emert et al. | |
| 5,160,647 | A * | 11/1992 | Odorisio et al. | 524/256 |
| 5,244,953 | A | 9/1993 | Odorisio et al. | |
| 6,426,324 | B1 | 7/2002 | Lai et al. | |
| 7,307,049 | B1 * | 12/2007 | DiBella et al. | 508/459 |

FOREIGN PATENT DOCUMENTS

| JP | 05155140 A * | 6/1993 |
|---|---|---|
| WO | WO 95/16765 | 6/1995 |

OTHER PUBLICATIONS

International Search Report and Written Opinion for PCT/US07/82519 dated Oct. 25, 2007 (9 pages).

* cited by examiner

*Primary Examiner* — Glenn Caldarola
*Assistant Examiner* — Jim Goloboy
(74) *Attorney, Agent, or Firm* — Joseph Suhadolnik

(57) ABSTRACT

Provided are compounds of formula

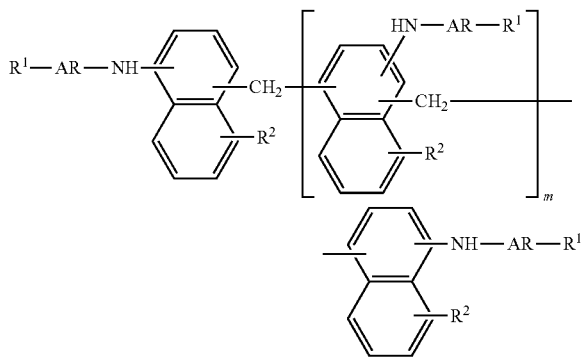

wherein $R^1$ is t-octyl, AR is phenyl, $R^2$ is an alkyl substituted carboxyl and m is 0, 1, or 2. Lubricating oils and hydraulic fluids comprising a polyol ester lubricant in combination with one or more compounds of formula I and methods for their use are also provided.

20 Claims, No Drawings

ANTIOXIDANTS FOR SYNTHETIC LUBRICANTS AND METHODS OF MANUFACTURE

CROSS REFERENCE TO RELATED APPLICATION

This application claims continuation priority to U.S. patent application Ser. No. 11/672,559 filed on Feb. 8, 2007, the disclosure of which is hereby incorporated by reference in its entirety.

FIELD

The present invention is generally related to antioxidants for lubricants and more particularly to an antioxidant for synthetic lubricants such as polyol ester lubricants.

BACKGROUND

Synthetic lubricants are generally specified in demanding high value applications such as stationary turbines, jet engines, hydraulic systems, and the like. Some synthetic lubricants are known as "polyol esters" and include compounds formed from monobasic fatty acids and polyhydric alcohols having a "neopentyl" structure. Representative alcohols useful for forming synthetic ester lubricants include neopentyl glycol, trimethylolpropane, pentaerythritol and dipentaerythritol. These alcohols are reacted to form esters with fatty acids generally having from about five to about twelve carbon atoms including: valeric, isopentanoic, hexanoic, heptanoic, octanoic, isooctanoic, 2-ethylhexanoic, pelargonic, isononanoic, decanoic and dodecanoic. The alcohols listed above generally have no beta-hydrogens and differ primarily in the number of hydroxyl groups available to form esters.

Depending on the fatty acids selected, i.e., same or different and numbers of carbon atoms, the properties of the polyol ester formed can be "designed" to provide a particular viscosity range, pour point, flash point and volatility as required for particular applications. Lower molecular weight acids, e.g., valeric, isopentanoic, etc., generally are used when flowability at low temperatures is important. Properties such as oxidative stability and resistance to hydrolysis may be enhanced by incorporation of acids having branching. In many applications, mixtures of both higher and lower molecular weight acids provide desirable properties. U.S. Pat. No. 4,440,657 discloses many simple esters, diesters and polyol esters suitable for use as lubricants.

In addition to selecting a synthetic lubricant based on its chemical structure, various additives are blended into the lubricant to enhance its oxidation resistance, disperse sludge formed, improve hydrolysis resistance, passivate metals, inhibit rust and the like. Antioxidants formed from polymerizing, for example, alkylated diphenyl amines and alkylated phenyl-α-naphthyl amines are widely used in many industrial applications including, but not limited to, thermoplastic resins, lubricants and hydraulic fluids to improve resistance to oxidation. U.S. Pat. No. 3,509,214 discloses that aromatic secondary naphthyl amines or N-arylnaphthylamines may be coupled or cross-coupled to form oligomers which, when present as additives in synthetic lubricants, enhance the resistance of the lubricants to high temperature oxidation.

Additional representative antioxidant additives are disclosed in U.S. Pat. No. 5,160,647 which discloses formaldehyde condensation products of alkylphenyl substituted-1-aminonaphthalenes. In this patent, all of the preparations of the disclosed compounds are prepared in solvent with the compound being isolated and purified as a solid material.

U.S. Pat. No. 3,492,233 discloses lubricant compositions containing dehydrocondensation products produced by chemically attaching an additive molecule such as an antioxidant, load-carrying agent, detergent, anticorrosion agent and the like to a lubricant molecule by heating the additive and an organic lubricant base fluid in the presence of an organic peroxide.

U.S. Pat. No. 6,426,324 discloses an antioxidant composition suitable for ester fluid lubricants formed from diphenylamines and N-aryl naphthylamines in the presence of an organic peroxide. In this disclosure, a reaction with a polyol ester lubricant base is disclosed, but is, according to the disclosure, a byproduct and ways to minimize the reaction between the amines and the polyol ester fluid are preferred.

Present preparations of antioxidants for lubricant fluids are multi-step and often require difficult and expensive separations and purifications. These current preparations add to the cost of preparing already expensive synthetic lubricants, such as polyol esters. If a compound having suitable antioxidant properties were available and a less complex, more efficient method for its preparation and incorporation into synthetic lubricants was provided, the art of stabilized polyol ester lubricants would be enhanced. Such a compound and a method for its preparation and incorporation into a synthetic polyol ester lubricant are provided herein below.

SUMMARY

An embodiment of the invention includes a compound of formula

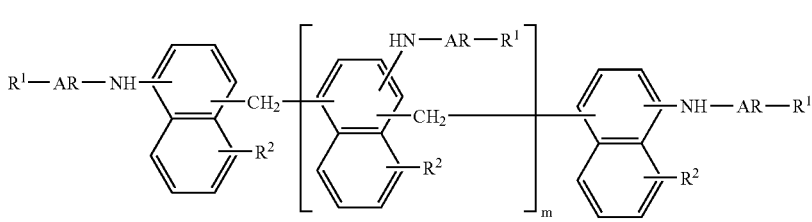

wherein $R^1$ is H or a linear or branched alkyl;

AR is phenyl, naphthyl, or phenanthryl;

in one embodiment, m=0; in another embodiment, m=1; and in a further embodiment, m=2; and $R^2$ is an alkyl substituted carboxyl.

Compounds of formula I are useful as antioxidant additives in synthetic lubricants, for example, polyol ester lubricants or hydraulic fluids.

In one aspect of the present invention, antioxidant additives are generally prepared by a condensation reaction of an alkylated phenyl-α-naphthyl amine (ALK PANA) with formaldehyde in the presence of a base lubricant. In one embodiment, a method of preparation includes mixing an alkylated phenyl-α-naphthyl amine, formaldehyde, glacial acetic acid, and a base lubricant, for example, a polyol ester. This mixture is then heated and stirred to cause a condensation reaction. Water is generated and distilled off. Following the removal of the water, the solution is heated and vacuum stripped to substantially remove residual water and acetic acid. The condensation reaction product, namely, an antioxidant, remains in the base lubricant.

The antioxidant and base lubricant mixture is then blended into the same or a compatible lubricant. Additional additives or additive packages are added as desired. Methods of the present invention that produce antioxidants from a condensation reaction of an alkylated phenyl-α-naphthyl amine with formaldehyde in the presence of synthetic lubricants, such as polyol ester lubricants, without additional isolation or work-up steps, greatly improve the efficiency of preparing these high value lubricants with an antioxidant additive. Previously, preparation of these types of antioxidant compounds required multiple steps to isolate and purify these types of compounds from the solvents in which they were synthesized.

DETAILED DESCRIPTION

An embodiment of the invention is a compound of formula assumption that the source of the $R^2$ is the carboxylate from the polyol ester, in one embodiment, $R^3$ is selected from the group consisting of linear or branched alkyl groups, i.e., hydrocarbons $C_nH_{2n+1}$ where n=4 to 11.

In the embodiment where the compound of formula I is formed in a base lubricant comprising acid esters of pentaerythritol, the organic acid of $R^2$ is generally selected from the group consisting of valeric, isopentanoic, hexanoic, octanoic, isooctanoic, 2-ethylhexanoic, pelargonic, isononanoic, decanoic, and dodecanoic.

In example 1, where the pentaerythritol tetraester was formed from straight or branched chain $C_5$-$C_{10}$ with an average chain length of about 6.3, $R^3$ would likely be a similar distribution of straight or branched chain $C_4$-$C_9$ alkyls. The $R^2$ carboxylate likely adds to the naphthyl ring by replacing a hydrogen atom at one or more of the 2, 4, 5, 7, and 8 positions. In Example 1, the mole ratio of carboxyl oxygen (as $O_2$) to N in the elemental analysis is about 0.85. This ratio suggests that there is a significant degree of transfer of a carboxyl moiety from the polyol ester to the nitrogen containing oligomer of formula I.

In a further aspect of the present invention, antioxidant additives are generally prepared by a condensation reaction of an alkylated phenyl-α-naphthyl amine (ALK PANA) with formaldehyde in the presence of a base lubricant. In one embodiment, a method of preparation includes mixing an alkylated phenyl-α-naphthyl amine, formaldehyde, glacial acetic acid, and a base lubricant, for example, a polyol ester.

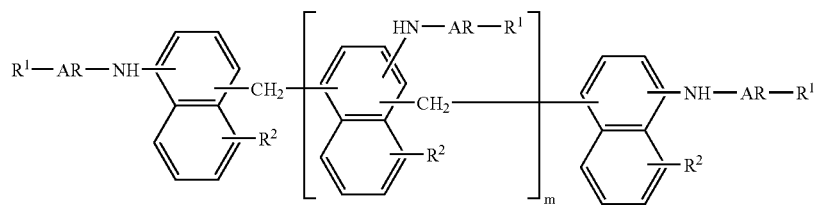

I wherein $R^1$ is H, or a linear or branched alkyl; AR is phenyl, naphthyl, or phenanthryl; in one embodiment, m is 0; in another embodiment, m is 1; and in a further embodiment, m is 2; and $R^2$ is an alkyl substituted carboxyl. In one embodiment, AR is phenyl. In another embodiment, $R^1$ is tertiary octyl. The compound of formula I includes the embodiment where $R^2$ is $R^3$—C(=O)O—. A further embodiment of the compound of formula I is where m is 0, 1, or 2, and the compound is a dimer (bis), trimer (tris) or tetramer (ter), respectively, of the alkylphenyl naphthyl amine coupled with formaldehyde.

The source of the $R^2$ group on the naphthyl ring is believed to be the polyol ester reaction medium. As shown in Examples 3 and 4, when a coupling reaction utilizing formaldehyde is conducted in methanol or glacial acetic acid as an alternative to conducting the same reaction in a polyol ester base lubricant, as shown in Example 1, there is no carbonyl absorbance in the Infrared spectrum in the products of either examples 3 or 4. Accordingly, it is believed that the source of the carbonyl absorbance in the compound of formula I when the compound is prepared using polyol ester as the reaction medium, is one of the carboxylate moieties from the base polyol ester. If the formaldehyde were the source of the carbonyl, it could be expected that this reaction would also occur where methanol or acetic acid was used as the solvent. In accord with the This mixture is then heated and stirred to cause a condensation reaction. Water is generated and distilled off. Following the removal of the water, the solution is heated and vacuum stripped to substantially remove residual water and acetic acid. The condensation product, namely an antioxidant, remains in the base lubricant.

In one embodiment, the compound of Formula I is prepared by mixing an alkylated phenyl-α-naphthyl amine, e.g., N-4-alkylphenyl-1-naphthlyamine, paraformaldehyde, glacial acetic acid and a polyol ester base lubricant. In one embodiment, the polyol is selected from the group consisting of neopentyl glycol, trimethylpropane, pentaerythritol, dipentaerythritol, and the like. In another embodiment, the polyol is esterified with an organic acid selected from the group consisting of valeric, isopentanoic, hexanoic, heptanoic, octanoic, isooctanoic, 2-ethylhexanoic, pelargonic, isononanoic, decanoic, and combinations thereof. During manufacturing, a hydrocarbon can be added to form an azeotrope to ease in evolving the water of reaction. In one embodiment, the hydrocarbon is one of saturated or aromatic hydrocarbons known to form azeotropes with water.

In another embodiment, the present invention includes a method for compounding a lubricating oil or hydraulic fluid formulation that includes an antioxidant additive. The method includes providing a lubricating oil or hydraulic fluid;

and blending a sufficient quantity of a compatible base polyol ester lubricant having an antioxidant, for example, the compound of formula I, prepared therein, so that the antioxidant achieves a preselected concentration. In a further embodiment, the lubricating oil is a polyol ester. In one embodiment, the resultant lubricating oil formulation substantially comprises a polyol ester. By reference to "substantially comprises a polyol ester" it is meant that the polyol ester comprises approximately at least about 90% or more by weight of the final formulation.

By reference to lubricant or hydraulic fluid formulation, one skilled in the art will recognize that this term encompasses a commercial formulation packaged for distribution in cans, drums or bulk containers. These lubricant formulations may include mineral oil based materials, synthetic lubricants, such as polyol esters, and compatible combinations thereof. These formulations may also include one or more of antioxidants, i.e., a compound of formula I, either solely or in combination with other compatible compounds, such as corrosion inhibitors, anti-wear agents, dispersants, metal passivants, and the like. Useful concentrations of the compound of formula I in the lubricant or hydraulic fluid formulation are generally between about 0.1 to about 10%. In one embodiment, a concentration for esterified pentaerythritol based formulations containing the compound of formula I is between about 1.5 to about 5.5 percent by weight. Other concentrations of the compound of formula I in lubricants or hydraulic fluids may be envisioned for particular applications and are to be considered within the scope of the present disclosure.

EXAMPLE 1

Preparation of Compound of Formula I

N-(4-t-octylphenyl)-1-naphthylamine (161.4 g/0.487 mole) was mixed with paraformaldehyde (95%) (10.78 g/0.341 mole); glacial acetic acid (21.15 g/0.352 mole); cyclohexane (50 g) and pentaerythritol tetraester (161.4 g) containing mixed $C_5$-$C_{10}$ carboxylates (with an average carbon chain length of about 6.3). The mixture was stirred and heated under a gentle nitrogen sparge to about 110° C. for about 90 minutes with the cyclohexane being distilled off as a water azeotrope into a Dean-Stark trap removing both water evolved and glacial acetic acid.

The aqueous acetic acid collected in the trap weighed 13.37 g and contained 4.83 g of acetic acid (determined by titration). The remaining 8.54 g includes the 6.14 g of water calculated for complete reaction as well as the water present in the paraformaldehyde and the glacial acetic acid reactants.

Next, the reaction mixed was vacuum stripped by heating to 140° C. under vacuum (to about 1 mm Hg) for 2 hours. Following the vacuum stripping, the reaction mixture was treated with a nitrogen sparge (about 10 L/Hr) for about one hour. The resultant viscous reddish liquid weighed 323.4 g with an acid no. of 0.07.

In order to further characterize the product from the above reaction, an aliquot of the viscous reddish liquid was triturated two times with aliquots of methyl alcohol with vigorous mixing. The resultant precipitate was then collected by vacuum filtration and further washed with several more aliquots of methanol. The resultant pink powder was dried under vacuum at 25° C. to constant weight providing a 45.7% yield (by weight) based on the reddish liquid. It is believed that the balance of the reddish liquid comprised lower molecular weight species with some degree of solubility in methanol. Infrared spectrum of the pink powder shows a carbonyl absorption at 1744 $cm^{-1}$, indicative of the presence of an ester carbonyl. Further, the elemental analysis found for this product, viz., C, 82.70; H, 8.88; N, 3.22; O, 6.24, shows a mole ratio of carboxyl oxygens to nitrogen of 0.85. These facts support the occurrence of a significant degree of transfer of a carboxyl moiety from the polyol ester to the nitrogen-containing oligomer via a substitution reaction.

Since the ALK PANA/formaldehyde mole ratio of reactants initially charged was 1.00/0.70, an average composition represented by a 3.33/2.33 mole ratio of ALK PANA/formaldehyde oligomer should theoretically result. By taking into account the contribution of the carboxylate moiety, assuming an average $C_5H_{11}C(=O)O-$ group, a molecular weight of about 1455 is calculated for the methanol-insoluble material as represented by an average formula of $C_{99.23}H_{124.88}N_{3.33}O_{5.66}$ which provides a calculated elemental analysis of C, 81.92; H, 8.65; N, 3.20; O, 6.22 comparing favorably with the "found" values state above.

GPC analysis of the isolated product was carried out in tetrahydrofuran solution and examined using a series of mixed pore size GPC columns. Detection of eluates was done using a photodiode array UV detector (Waters/Alliance 2996) with molecular weight calibration using polystyrene standards. The GPC values of $M_n$=1293, $M_w$=1558, where D=1.20.

EXAMPLE 2

Condensation of N-phenyl-1-naphthylamine with Formaldehyde in Polyol Ester Solvent Following the procedure of Example 1, N-phenyl-1-naphthylamine (150.3 g/0.685 mole) was mixed with paraformaldehyde (95%) (15.2 g/0.481 mole), glacial acetic acid (31.1 g/0.518 mole), 62 g cyclohexane and pentaerythritol tetraester containing mixed $C_5$-$C_{10}$ carboxylates. The mixture was stirred with heating and then vacuum stripped. The resultant product was a viscous liquid weighing 321.0 g with an acid number of 0.07. The methanol-insoluble component of this preparation was isolated as a beige powder providing a yield by weight of 35.3%. The infrared spectrum of the isolated product also showed an absorbance at 1744 $cm^{-1}$, characteristic of carbonyl oxygen. Elemental analysis found for this product, viz., C, 82.74; H, 6.74; N, 4.69, O, 6.44 indicates a mole ratio of carboxyl oxygens to nitrogen as 0.60. Proceeding similarly to Example 1, a molecular weight of ca. 987 is calculated for this methanol-insoluble material as represented by an average formula of $C_{67.67}H_{63.33}N_{3.33}O_{6.48}$. GPC data showed values of $M_n$=965, $M_w$=1076 where D=1.12.

EXAMPLE 3

Condensation of N-(4-t-octylphenyl-1-naphthylamine) with Formaldehyde in Methanol Following the procedure listed in U.S. Pat. No. 5,160,647, Example 1, N-(4-t-octylphenyl)-1-naphthylamine (33.1 g/0.1 mole) suspended in methanol (150 ml) acidified with 98% $H_2SO_4$ (10.2 g/ca. 0.1 mole) was mixed with 37.6% aqueous formaldehyde (4.0 g/0.05 mole) and heated to reflux for about 2 hours. After an extended workup as described in the referenced patent, a beige product was obtained in 76.8% yield (calculated as the dimer) for which no carbonyl absorption in the Infrared spectrum was present. Analysis calculated for the dimer $C_{49}H_{58}N_2$, C, 87.19; H, 8.66; N, 4.15. Found C, 87.26; H, 8.61; and N, 4.07. GPC analysis showed Mn=996, Mw=1076 and a D=1.08, which indicates mostly a dimethylene-tris ALK PANA composition.

EXAMPLE 4

Condensation of N-(4-t-octylphenyl-1-naphthylamine) with Formaldehyde in Glacial Acetic Acid These examples (A-C) illustrate preparations using several mole ratios of the nitrogen containing naphthylamine to formaldehyde.

A) mole ratio 1.0/0.5 (amine/formaldehyde). N-(4-t-octylphenyl)-1-naphthylamine (22.97 g/0.0693 mole) was mixed with stirring into 45 g of glacial acetic acid. This mixture was heated to 65° C. with stirring to dissolve the amine. 95% paraformaldehyde (1.09 g/0.0345 mole) was added and rapidly dissolved. A precipitate, accompanied by an exotherm to 75° C., developed in less than one minute. The reaction mixture was allowed to cool to room temperature and the insoluble precipitate was collected, triturated with methanol in a Waring Blendor®, suction filtered, washed with methanol and dried to constant weight at 80° C. 15.83 g of a beige powder was collected representing a 67.6% yield based on the weight of the reactants. Analysis calculated for $C_{49}H_{58}N_2$; Calculated-C, 86.94; H, 8.62; N, 4.16; and Found-C, 87.19; H, 8.66; N, 4.15. GPC analysis showed $M_n$ of 918, a $M_w$ of 1009 and a D value of 1.10. The GPC result is substantially the same as that obtained with the product of Example 3. No carbonyl absorbance is present in the infrared spectrum.

B) mole ratio 1.0/0.67 (amine/formaldehyde). N-(4-t-octylphenyl)-1-naphthylamine (22.97 g/0.0693 mole) was mixed with stirring into 45 g of glacial acetic acid. This mixture was heated to 65° C. with stirring to dissolve the amine. 95% paraformaldehyde (1.53 g/0.0483 mole) was added and rapidly dissolved. A precipitate, accompanied by an exotherm to 75° C., developed in less than one minute. The reaction mixture was allowed to cool to room temperature and the insoluble precipitate was collected, triturated with methanol in a Waring Blendor®, suction filtered, washed with methanol and dried to constant weight at 80° C. 18.99 g of a beige powder was collected representing an 81.1% yield based on the weight of the reactants. Analysis calculated for $C_{77}H_{87}N_3$; Calculated-C, 87.69; H, 8.32; N, 3.99; and Found-C, 87.10; H, 8.53; N, 4.00. GPC analysis showed $M_n$ of 1067, a $M_w$ of 1334 and a D value of 1.25. No carbonyl absorbance is present in the infrared spectrum.

C) mole ratio 1.0/1.0 (amine/formaldehyde). N-(4-t-octylphenyl)-1-naphthylamine (22.97 g/0.0693 mole) was mixed with stirring into 45 g of glacial acetic acid. This mixture was heated to 65° C. with stirring to dissolve the amine. 95% paraformaldehyde (2.18 g/0.690 mole) was added and rapidly dissolved. A precipitate, accompanied by an exotherm to 75° C., developed in less than one minute. The reaction mixture was allowed to cool to room temperature and the insoluble precipitate was collected, triturated with methanol in a Waring Blendor®, suction filtered, washed with methanol and dried to constant weight at 80° C. 21.4 g of a beige powder was collected representing a 91.5% yield base on the weight of the reactants. Analysis calculated for $C_{25}H_{29}N$, (repeating unit); Calculated-C, 87.40; H, 8.52; N, 4.08; and Found-C, 86.94; H, 8.47; N, 3.98. GPC analysis showed $M_n$ of 1565, a $M_w$ of 2548 and a D value of 1.63. No carbonyl absorbance is present in the infrared spectrum.

Examples 4B) and C) substantially confirm, in accordance with a condensation oligomerization system, the expected formation of products of higher average molecular weights together with a greater distribution, i.e., a higher D value, of products comprising these averages.

EXAMPLE 5

High Temperature Stabilization of Lubricating Oil

Aliquots of the compounds prepared in Examples 1, 2, 3, and 4 were used to make industrial lubricant formulations having a composition of 95.29 weight % ester, 2.35 weight % other additives, and variable weight % of the compounds of examples 1, 2, 3, and 4 as listed in Table 1 below. Oxidation Corrosion (OCS) testing was carried out using Federal Test Method 5308 under conditions of 400° C., 72 hours, 5 liters/hour air flow using test metals of copper, aluminum, steel, silver, and zinc. Table 1 also lists: increase in viscosity; the acid number; the sludge generated; and the corrosion in $mg/cm^2$ in accordance with the standard test for the several metals with the examples at several concentrations in a polyol ester lubricant. A standard commercial lubricant (Vanlube 9317) and an aliquot of the same polyol ester without any additive package are respectively used as a positive and a negative control. The unbracketed values, e.g., "37.8" for Zn in the Negative control, indicate weight loss while the bracketed values, e.g., "(0.062)" for Cu in the Negative control, indicate weight gain.

TABLE 1

| Ex. # | Conc. % added. | Visc. % increase | Acid No. | Sludge (mg.) | Cu mg/cm | Al mg/cm | St mg/cm | Zn mg/cm | Ag mg/cm |
|---|---|---|---|---|---|---|---|---|---|
| Neg. control | None | 139.9 | 7.74 | 37.0 | (0.062) | (0.023) | (0.023) | 37.8 | (0.101) |
| 1 | 2.12 | 9.44 | 0.60 | 0.50 | 0 | (0.008) | (0.039) | 0.016 | 0.039 |
| 1 | 2.35 | 10.85 | 0.46 | 0.50 | (0.008) | (0.008) | (0.008) | 0.016 | 0.008 |
| 2 | 1.42 | 6.95 | 0 | 48.9 | (0.194) | (0.046) | (0.046) | (0.023) | (0.039) |
| 2 | 2.35 | 7.53 | 0.54 | 246 | (0.029) | (0.023) | (0.047) | (0.031) | (0.093) |
| 3 | 2.10 | 5.33 | 1.00 | 7.7 | (0.008) | 0.008 | (0.023) | (0.023) | 0.054 |
| 4A | 2.10 | 6.24 | 0.55 | 2.8 | 0.008 | (0.008) | (0.008) | 0 | 0 |
| 4B | 2.10 | 7.27 | 0.67 | 9.0 | (0.008) | 0.008 | 0.008 | 0.016 | 0.023 |
| 4C | 2.10 | 5.65 | 0.64 | 1.7 | (0.016) | (0.023) | (0.062) | (0.062) | (0.062) |
| Pos. control | 2.35 | 6.18 | 0.02 | 1.3 | 0.046 | (0.008) | (0.016) | 0.016 | 0 |

The results for example 1 for formula I of the invention compare favorably to the results of a current commercial standard (Vanlube 9317) given above as "Pos. control" determined under similar conditions.

Although the invention herein has been described with reference to particular embodiments, it is to be understood

What is claimed is:

1. A compound of formula

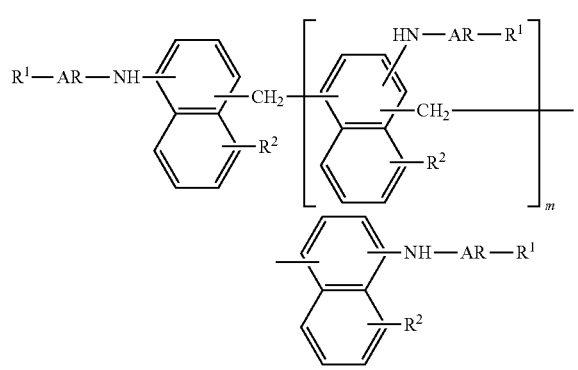

I wherein $R^1$ is t-octyl;
AR is phenyl;
m is 0, 1, or 2; and
$R^2$ is an alkyl substituted carboxyl.

2. The compound of claim 1 wherein m=0.
3. The compound of claim 1 wherein m=1.
4. The compound of claim 1 wherein m=2.
5. The compound of claim 1 wherein $R^2$ is $R^3$—C(=O)O—.
6. The compound of claim 5 wherein $R^3$ is selected from the group consisting of linear or branched alkyl groups.
7. The compound of claim 6 wherein the linear or branched alkyl comprises $C_nH_{2n+1}$ wherein n is from 4 to 11.
8. The compound of claim 6 wherein the linear or branched alkyl group is derived from an organic acid ester of pentaerythritol, the organic acid being selected from the group consisting of valeric, isopentanoic, hexanoic, octanoic, isooctanoic, 2-ethylhexanoic, pelargonic, isononanoic, decanoic, dodecanoic, and combinations thereof.
9. The compound of claim 7 wherein $R^3$ is isobutyl.
10. A lubricant or hydraulic fluid composition comprising an admixture of:
from about 1.5 to about 5% (w/w) of a compound of formula I;
up to about 5% of an additive package selected from the group consisting of corrosion inhibitors, anti-wear agents, dispersants, metal passivants, and combinations thereof; and
the balance being a base material selected from the group consisting of mineral oil based materials, synthetic lubricants, polyol esters, and combinations thereof.
11. The lubricant or hydraulic fluid composition of claim 10, wherein the base material selected is a polyol ester is formed from a polyol selected from the group consisting of neopentyl glycol, trimethylolpropane, pentaerythritol and dipentaerythritol; the polyol being esterified with an organic acid selected from the group consisting of valeric, isopentanoic, hexanoic, heptanoic, octanoic, isooctanoic, 2-ethylhexanoic, pelargonic, isononanoic, decanoic, dodecanoic and combinations thereof.
12. The lubricant or hydraulic fluid of claim 11 wherein the polyol is pentaerythritol, the polyol being esterified with an acid selected from the group consisting of valeric, isopentanoic, hexanoic, octanoic, isooctanoic, 2-ethylhexanoic, pelargonic, isononanoic, decanoic, dodecanoic and combinations thereof.
13. The lubricant or hydraulic fluid of claim 12 wherein the pentaerythritol is esterified with $C_5$-$C_{10}$ straight chain or branched acids having an average carbon chain length of about 6.3.
14. The lubricant or hydraulic fluid of claim 10 having a viscosity increase of about ten percent or less after testing according to Federal Test Method 5308.
15. The lubricant or hydraulic fluid of claim 10 having an acid number increase of no more than about one after testing according to Federal Test Method 5308.
16. A method of lubricating an apparatus selected from the group consisting of a stationary turbine, a jet engine, and a hydraulic system, the method comprising:
providing a fluid material comprising an admixture between about 0.1 and 10% (w/w) of a compound of formula I, an additive package selected from the group consisting of corrosion inhibitors, anti-wear agents, dispersants, metal passivants, and combinations thereof, the balance being a base material selected from the group consisting of mineral oil based materials, synthetic lubricants, polyol esters, and combinations thereof; and
placing the fluid material in the system.
17. The method of claim 16, wherein the providing step further comprises selecting a polyol ester base lubricant formed from a polyol selected from the group consisting of neopentyl glycol, trimethylolpropane, pentaerythritol, and dipentaerythritol; the polyol being esterified with an organic acid selected from the group consisting of valeric, isopentanoic, hexanoic, heptanoic, octanoic, isooctanoic, 2-ethylhexanoic, pelargonic, isononanoic, decanoic, dodecanoic, and combinations thereof.
18. The method of claim 17 wherein the providing step comprises selecting a polyol ester base lubricant formed from pentaerythritol and $C_5$-$C_{10}$ straight chain or branched acids having an average carbon chain length of about 6.3.
19. A packaged commercial lubricant or hydraulic fluid composition for distribution comprising:
between about 0.1 and 10% (w/w) of a compound of formula I;
an additive package selected from the group consisting of corrosion inhibitors, anti-wear agents, dispersants, metal passivants, and combinations thereof and the balance being a base material selected from the group consisting of mineral oil based materials, synthetic lubricants, polyol esters, and combinations thereof; and
a container selected from the group consisting of cans, drums or bulk containers.
20. The packaged composition of claim 19, wherein the base material selected is a polyol ester is formed from a polyol selected from the group consisting of neopentyl glycol, trimethylolpropane, pentaerythritol and dipentaerythritol; the polyol being esterified with an organic acid selected from the group consisting of valeric, isopentanoic, hexanoic, heptanoic, octanoic, isooctanoic, 2-ethylhexanoic, pelargonic, isononanoic, decanoic, dodecanoic and combinations thereof.

* * * * *